United States Patent [19]

Vogt

[11] 4,208,585
[45] Jun. 17, 1980

[54] APPARATUS FOR FOCUSING ELECTROMAGNETIC RADIATION ON A SAMPLE

[75] Inventor: Henning Vogt, Cologne, Fed. Rep. of Germany

[73] Assignee: Leybold-Heraeus GmbH, Cologne, Fed. Rep. of Germany

[21] Appl. No.: 940,138

[22] Filed: Sep. 6, 1978

[30] Foreign Application Priority Data

Sep. 7, 1977 [DE] Fed. Rep. of Germany ....... 2740183

[51] Int. Cl.² .................. H01J 39/48; G02B 7/18
[52] U.S. Cl. .................. 250/423 P; 250/287; 250/288; 356/244
[58] Field of Search .................. 350/91, 296, 294; 356/317, 318, 244; 250/423 P, 289, 287, 281; 219/121 L

[56] References Cited

U.S. PATENT DOCUMENTS

| 3,644,731 | 2/1972 | Eloy | 250/289 |
| 3,813,544 | 5/1974 | Franzen et al. | 250/281 |
| 4,017,163 | 4/1977 | Glass | 350/294 |

FOREIGN PATENT DOCUMENTS 129373 1/1978 Fed. Rep. of Germany ............ 356/85

OTHER PUBLICATIONS

Eloy and Dumas, "Methodes Paysiques d'Analyse (GAMS)", Jul.-Sep. 1966, pp. 251-257.
R. A. Bingham and P. L. Salter, "International Jour. of Mass Spect. and Ion Physics," 21 (1976), p. 133.

*Primary Examiner*—Jon W. Henry
*Attorney, Agent, or Firm*—Spencer & Kaye

[57] ABSTRACT

Apparatus for directing a beam of electromagnetic radiation onto a sample by focusing and deflecting the radiation, employing a spherical mirror for focusing and deflecting the radiation onto the sample.

4 Claims, 1 Drawing Figure

U.S. Patent  Jun. 17, 1980  4,208,585
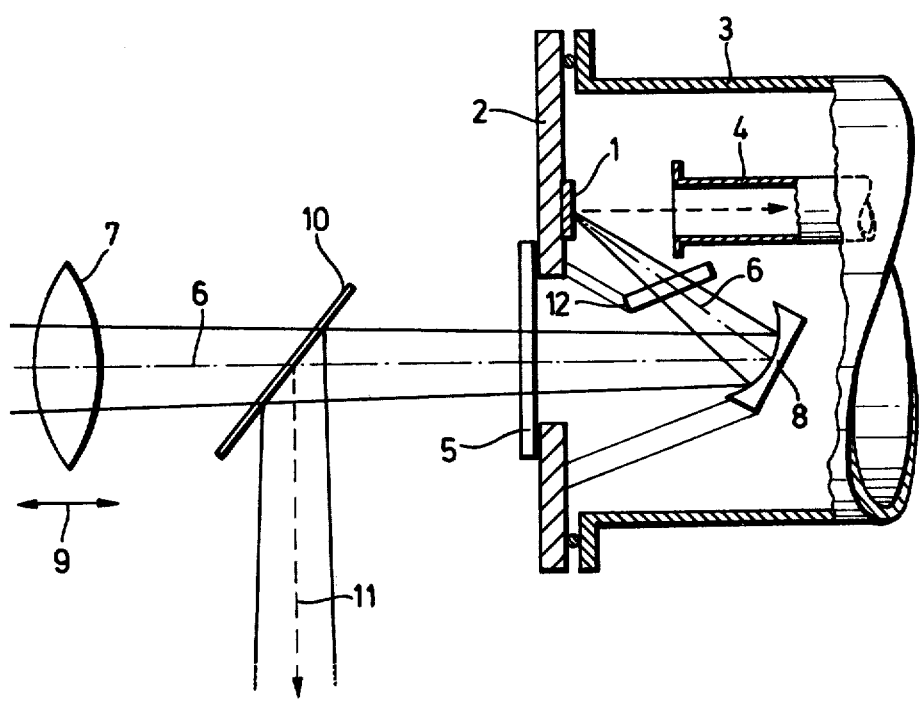

APPARATUS FOR FOCUSING ELECTROMAGNETIC RADIATION ON A SAMPLE

BACKGROUND OF THE INVENTION

The present invention relates to an apparatus for focusing electromagnetic, preferably pulsed laser, radiation, onto a sample with the aid of an optical component for focusing the radiation and a mirror for reflecting the radiation.

It is known to use laser radiation, in the microanalysis of materials, to evaporate the sample material and to produce plasma. In such procedures, it is desirable to focus the radiation to extremely small areas of the order of magnitude of a few microns, in order to make it possible to obtain not only information about the chemical composition of the sample material but also about its structure. The sample is generally accommodated in a vacuum chamber in which the devices for analyzing the evaporated sample material, e.g. a time of flight mass spectrometer among others, are disposed. If the sample is very thin, e.g. $0.1$–$0.5\mu$, focusing of the laser beam on the side of the sample facing the mass spectrometer may be effected through the sample. If the sample is thicker and not transparent to the laser radiation the radiation must be introduced into the vacuum chamber, for example via a window, and must there be deflected onto the sample with the aid of a mirror.

The present invention relates to such an apparatus for focusing the reflected beam of electromagnetic radiation onto a sample.

A paper by J. F. Eloy and J. L. Dumas in "Methodes Physiques d'Analyse (GAMS)", July through September 1966, at pages 251 et seq., discloses the introduction of laser radiation into a vacuum chamber through a window, the provision of a lens in the vacuum chamber for focusing a beam of the laser radiation and the deflection of this focused laser beam in the direction of the sample with the aid of a planar mirror. This arrangement has the drawback that the lens must have a long focal length since it is arranged relatively far away from the sample. This makes it impossible to produce focal spots of less than $20\mu$ diameter.

It is further known, as disclosed in a paper by R. A. Bingham and P. L. Salter in "International Journal of Mass Spectroscopy and Ion Physics", 21 (1976), page 133, to initially deflect the laser beam in the direction of the sample with the aid of a planar mirror and to arrange a lens system between this planar mirror and the sample. This prior art arrangement has the advantage that it can operate with lenses having short focal lengths, but it also has the drawback that relatively large optical components must be arranged in the immediate vicinity of the sample, which complicates the structure of the device as a whole. Moreover, when operating with various laser light wavelengths, the lens system must be achromatic, i.e. it must be independent of the wavelength of the laser radiation. Such an achromatic system, however, is very expensive.

SUMMARY OF THE INVENTION

It is an object of the present invention to provide an apparatus which can produce extremely small focal spots on the sample with a reflected beam using extremely simple means.

This is accomplished, according to the present invention, by providing, in apparatus of the type described above, a spherical mirror for both focusing and deflecting the radiation. The significant advantage of this arrangement is that the mirror can be relatively small, which saves space and which enables it to be accommodated in the immediate vicinity of the sample. Focusing of the laser light on the sample can therefore take place with a very short focal length so that it is possible to obtain beam constrictions or focal spots, respectively, with very small diameters. An expensive achromatic system in the immediate vicinity of the sample is no longer necessary since the focusing action of a spherical mirror on electromagnetic radiation is independent of wavelength.

In further accordance with the invention, a lens with a long focal length is placed ahead of the spherical mirror. Displacement of this lens effects axial displacement of the focal spot and thus accurate adjustment of the focal spot on the surface of the sample. Such a device is necessary if the position of the sample cannot be adjusted. If the system operates with laser beams of different wavelengths, this lens, nevertheless must be an achromatic lens, but it may be disposed outside the vacuum-tight housing so that as few components as possible are present in the vicinity of the sample.

Passage of the laser radiation through the window and deflection of the laser beam at the spherical mirror will, however produce errors. Therefore, in further accordance with the present invention a further glass plate is arranged between the spherical mirror and the sample. Such a simple glass plate, which requires only little space, can easily be arranged to correct imaging errors.

Finally a beam divider may be disposed between the spherical mirror and the long focal length lens so as to establish a coaxial relationship between reflected light illumination for the sample and an optical system for observation purposes.

BRIEF DESCRIPTION OF THE DRAWING

The sole FIGURE is a simplified, elevational cross-sectional view of a preferred embodiment of the invention.

DESCRIPTION OF THE PREFERRED EMBODIMENTS

In the illustrated embodiment, a sample 1 is to be evaporated with the aid of laser radiation. The sample 1 is mounted at a cover flange 2 with which the housing 3 can be sealed in a vacuum-tight manner. Any desired means for analyzing the evaporated sample material, only a part of a travel time mass spectrometer 4 being shown, are accommodated in the housing 3.

The cover flange 2 also has a window 5, preferably of quartz glass, which serves to provide passage for the laser light beam into the housing 3. While the axis 6 of the laser light beam is shown, the laser light source itself, which can be of known design, is not shown.

In the illustrated embodiment, the laser light beam first passes through a lens 7 having relatively long focal length and converging the laser beam only slightly. This slightly converged laser beam passes through the window 5 and impinges on the spherical mirror 8 which not only deflects the laser light in the direction toward sample 1 but also focuses it to a spot on the surface of the sample 1.

The mirror 8 does not take up very much space so that it can be accommodated relatively close to sample 1. It focal length may therefore be selected to be relatively short so that focal spots with very small diameters, e.g. less than 5μ, can be produced on the surface of the sample 1. Accurate focusing of the focal spot on the surface of the sample 1 can be effected by axial displacement of the lens in the directions of double arrow 9.

Between the lens 7 and the window 5 there is disposed a beam divider 10. With this beam divider an illumination for sample 1 and an optical system for observation purposes can be arranged along axis in 11 and beside axis 6 of the main beam, coming from the laser. Both beams—illumination beam and laser beam—are collinear between divider 10 and sample 1.

Finally, in the illustrated embodiment, a glass plate 12 is disposed between the sample 1 and the spherical mirror 8. Especially astigmatic errors due to deflection at the spherical mirror 8 can be compensated with this glass plate, if it is arranged in an non perpendicular position to axis 6, as shown in the FIGURE 10.

The manner of mounting the individual optical components 8 and 12 in the housing 3 is not shown. It is advisable, however, to fasten them to the cover flange 2 so that they can be removed from the housing 3 as a unit with the flange.

It will be understood that the above description of the present invention is susceptible to various modifications, changes and adaptations, and the same are intended to be comprehended within the meaning and range of equivalents of the appended claims.

What is claimed is:

1. In apparatus for directing a beam of electromagnetic radiation onto a sample by focusing and deflecting the radiation, the improvement comprising: a spherical mirror disposed for focusing and deflecting the radiation onto the sample; an axially displaceable lens with a long focal length disposed ahead of said sphereical mirror in the beam path; and a vacuum-tight housing for accommodating the sample and a window in a wall of said housing for the passage of the radiation, with said spherical mirror being disposed inside said housing and said lens being disposed outside said housing, and wherein said housing is provided with a cover flange hermetically sealing said housing, said window is carried by said cover flange for the passage of the radiation into the housing, and the sample and said mirror are mounted on said cover flange.

2. An arrangement as defined in claim 1 further comprising a glass plate for correcting imaging errors disposed between said spherical mirror and the sample.

3. An arrangement as defined in claim 1 or 2 further comprising a beam divider disposed between said lens and said spherical mirror.

4. An arrangement as defined in claim 1 wherein the radiation is pulsed laser radiation.

* * * * *